US010576183B2

(12) United States Patent
Kweon et al.

(10) Patent No.: US 10,576,183 B2
(45) Date of Patent: Mar. 3, 2020

(54) COCOON-BASED VASCULAR PATCH AND MANUFACTURING METHOD THEREOF

(71) Applicant: REPUBLIC OF KOREA (MANAGEMENT:RURAL DEVELOPMENT ADMINISTRATION), Jeonju-si, Jeollabuk-do (KR)

(72) Inventors: Hae Yong Kweon, Suwon-si (KR); You Young Jo, Jeollabuk-do (KR); Kwang Gill Lee, Suwon-si (KR); Hyun Bok Kim, Jeollabuk-do (KR); Heui Sam Lee, Suwon-si (KR); Joo Hong Yeo, Suwon-si (KR); Seok Woo Kang, Hwaseong-si (KR)

(73) Assignee: Republic of Korea (Management:Rural Development Administration), Jeonju-si, Jeollabuk-do (KR)

( * ) Notice: Subject to any disclaimer, the term of this patent is extended or adjusted under 35 U.S.C. 154(b) by 199 days.

(21) Appl. No.: 15/515,772

(22) PCT Filed: Sep. 18, 2015

(86) PCT No.: PCT/KR2015/009830
§ 371 (c)(1),
(2) Date: Mar. 30, 2017

(87) PCT Pub. No.: WO2016/072614
PCT Pub. Date: May 12, 2016

(65) Prior Publication Data
US 2017/0304498 A1 Oct. 26, 2017

(30) Foreign Application Priority Data
Nov. 5, 2014 (KR) ........................ 10-2014-0152646

(51) Int. Cl.
| A61L 27/36 | (2006.01) |
| A61K 9/70 | (2006.01) |
| A61K 35/63 | (2015.01) |
| A61L 27/44 | (2006.01) |
| A61L 27/50 | (2006.01) |
| A61L 27/56 | (2006.01) |
| A61F 2/00 | (2006.01) |

(52) U.S. Cl.
CPC ............ *A61L 27/3637* (2013.01); *A61K 9/70* (2013.01); *A61K 35/63* (2015.01); *A61L 27/3604* (2013.01); *A61L 27/3691* (2013.01); *A61L 27/44* (2013.01); *A61L 27/507* (2013.01); *A61L 27/56* (2013.01); *A61F 2/0063* (2013.01)

(58) Field of Classification Search
None
See application file for complete search history.

(56) References Cited

U.S. PATENT DOCUMENTS

| 2009/0133814 A1 | 5/2009 | Lee |
| 2009/0214649 A1* | 8/2009 | Gazit ................... A61L 27/225 424/484 |
| 2014/0193466 A1 | 7/2014 | Lawrence et al. |
| 2014/0288638 A1 | 9/2014 | Knight et al. |
| 2015/0239944 A1 | 8/2015 | Teuschl et al. |

FOREIGN PATENT DOCUMENTS

| EP | 2712955 A1 | 4/2014 |
| JP | 06-166850 | * 6/1994 |
| JP | 2011-147790 A | 8/2011 |
| KR | 10-0315168 B1 | 11/2001 |
| KR | 10-0667515 B1 | 1/2007 |
| KR | 10-2013-0051602 A | 5/2013 |

OTHER PUBLICATIONS

Chen (Acta Biomaterialia (2012), vol. 8, pp. 2620-2627).*
Zhao (Polymer (20050, vol. 46, pp. 9192-9201).*
S. W. Cho et al., "Development of Vascular Patch Using Mesenchymal Stem Cell and Biodegradable Matrix", KSBB, Proceedings of Current Biotechnology and Bioengineering (XII), Apr. 2003, pp. 98-100.

* cited by examiner

Primary Examiner — Susan Hoffman
(74) Attorney, Agent, or Firm — Rabin & Berdo, P.C.

(57) ABSTRACT

Disclosed herein are a cocoon-based, vascular patch and a method for manufacturing the same. The cocoon-based, vascular patch is manufactured by dividing a cocoon into two or more fragments in a predetermined form, the cocoon having a shell having a predetermined thickness. The cocoon-based vascular patch can be relatively simply manufactured in a more cost efficient manner than conventional vascular patches, and has excellent cell growth potential and biocompatibility.

6 Claims, 7 Drawing Sheets

COCOON-BASED VASCULAR PATCH AND MANUFACTURING METHOD THEREOF

TECHNICAL FIELD

The present invention relates to a vascular patch using a cocoon, and a method for manufacturing the same. More particularly, the present invention relates to a cocoon-based vascular patch that is biocompatible, effectively maintains vessel diameters, and promotes the growth of vascular endothelial cells at vessel defects, and a method for manufacturing the same.

BACKGROUND ART

During surgical operation in the oral and maxillofacial region, such as neck dissection, oral tumor removal, maxillofacial trauma surgery, blood vessels may be injured, particularly at the lesion adjacent thereto. When injured, blood vessels are treated by ligation or direct closure. For large blood vessels, such as the carotid artery, which is frequently met upon neck dissection, ligation is reported to frequently cause various complications, such as cerebral infarction. In addition, direct closure of severely injured blood vessels may induce angiostenosis, leading to cerebral infarction, or neurological complications due to vascular dysfunction. Hence, development of methods and materials by which injured vessels can be simply treated for their functional maintenance and regeneration are clinically needed.

Designed to reduce the complications caused by direct closure, such as angiostenosis, occlusions, etc., vascular patches are applied to injured vessels in the cardiovascular system. Many reports on the comparison between treatment of injured blood vessels with direct closure and vascular patches have predominantly shown better results from vascular patch treatment than direct closure.

However, conventional vascular patches made of synthetic polymers such as PET, ePTFE, Gore-Tex, etc., cannot perform vascular functions for a long period of time because they are apt to cause thrombotic angiostenosis and vascular calcification due to their very poor biocompatibility. Also, the poor biocompatibility is a cause of inflammation or tissue necrosis. Further, such vascular patches are expensive. Most vascular patches are adapted for cardiac vessels, and are limitedly applied to relatively thin blood vessels in the oral and maxillofacial region.

Research has been ongoing into vascular patches that are made of biocompatible materials and which can maintain vascular morphology without causing occlusion.

As far as relevant techniques are concerned, reference may be made to the 2003 academic publication of the Korean Society for Biotechnology and Bioengineering (Development of Vascular Patch Using Mesenchymal Stem Cell and Biodegradable Matrix), and Korean Patent Unexamined Application Publication No. 10-2013-0051602 (titled "3D Silk fibroin fiber characterized in dermal substitution and method of preparation for the same").

DISCLOSURE

Technical Problem

It is an object of the present invention to provide a cocoon-based vascular patch that is sufficiently biocompatible that it can stimulate endothelial cell growth without the tissues having foreign body reactions nor inflammations, thus regenerating vessel walls, and that it can prevent the occurrence of stenosis, thus effectively maintaining blood circulation and vessel diameter constant, and a method for manufacturing the same.

It is an object of the present invention to provide a biocompatible cocoon-based vascular patch that can be relatively simply manufactured in a more cost efficient manner than conventional vascular patches, and a method for manufacturing the same.

Embodiments of the present invention will be described in detail with reference to the accompanying drawings. These embodiments will be described in detail in order to allow those skilled in the art to practice the present invention. It should be appreciated that various embodiments of the present invention are different, but are not necessarily exclusive. For example, specific shapes, configurations, and characteristics described in an embodiment of the present invention may be implemented in another embodiment without departing from the spirit and the scope of the present invention. In addition, it should be understood that the positions and arrangements of individual components in each disclosed embodiment may be changed without departing from the spirit and the scope of the present invention. Therefore, the detailed description provided below should not be construed as being restrictive. In addition, the scope of the present invention is defined only by the accompanying claims and their equivalents if appropriate.

Technical Solution

In order to accomplish the above objects, an aspect of the present invention provides a cocoon-based vascular patch, prepared by dividing a cocoon into two or more fragments in a predetermined form, the cocoon having a shell with a first thickness.

In one exemplary embodiment of the present invention, each of the fragments may be delaminated into a lamellar fragment with a second thickness, the second thickness being smaller than the first thickness.

In another exemplary embodiment of the present invention, the lamellar fragment with a second thickness may be an inner, mid, or outer stratum of the cocoon.

In another exemplary embodiment of the present invention, the lamellar fragment may be sterilized and packed.

In accordance with another aspect thereof, the present invention provides a method for manufacturing a cocoon-based vascular patch, comprising a first step of dividing a cocoon into two or more fragments in a predetermined form, the cocoon having a shell with a first thickness, and a second step of delaminating each of the fragments into a lamellar fragment with a second thickness, the second thickness being less than the first thickness.

In an exemplary embodiment of the present invention, the method may further comprise a third step of packing the fragments of the second thickness prepared in the second step.

In another exemplary embodiment of the present invention, the method may further comprise conducting at least one round of sterilization before or after each step.

In another exemplary embodiment of the present invention, the lamellar fragment with a second thickness may be an inner, mid, or outer stratum of the cocoon.

Advantageous Effects

The cocoon-based vascular patch of the present invention needs not to be removed after it is applied for the closure of vessel defects, exhibits excellent cell growth potential and maintains the diameter of the vessel, with the consequent effective blood circulation through the vessel. In addition, the cocoon-based vascular patch can be prepared easily and thus in a cost-efficient manner, compared to conventional vascular patches.

BEST MODE

Unless otherwise defined, all terms used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Conventional artificial patches are mostly made of polyester or PTFE. When used in the body, such artificial patches have the likelihood of causing infection, post-anastomotic vasodilatation, thrombotic occlusion, and hemorrhage through stitch holes. The surgical operation with such artificial patches should be made in consideration of properties of the material. Gore-Tex patches, recently developed by W.L. Gore (Flagstaff, Ariz., USA), have not yet been proven for safety to long-term vasodilatation or neointimal hyperplasia. If failed, the patches might cause toxicity to the body or remain as foreign matter in the body when used for a long period of time.

Leading to the present invention, intensive and thorough research into a vascular patch, conducted by the present inventor, resulted in the finding that a fragment prepared from a cocoon is biocompatible and useful as a vascular patch because it exhibits excellent cell adhesion and growth potential upon in vivo application without causing inflammation reactions.

Figure 1:
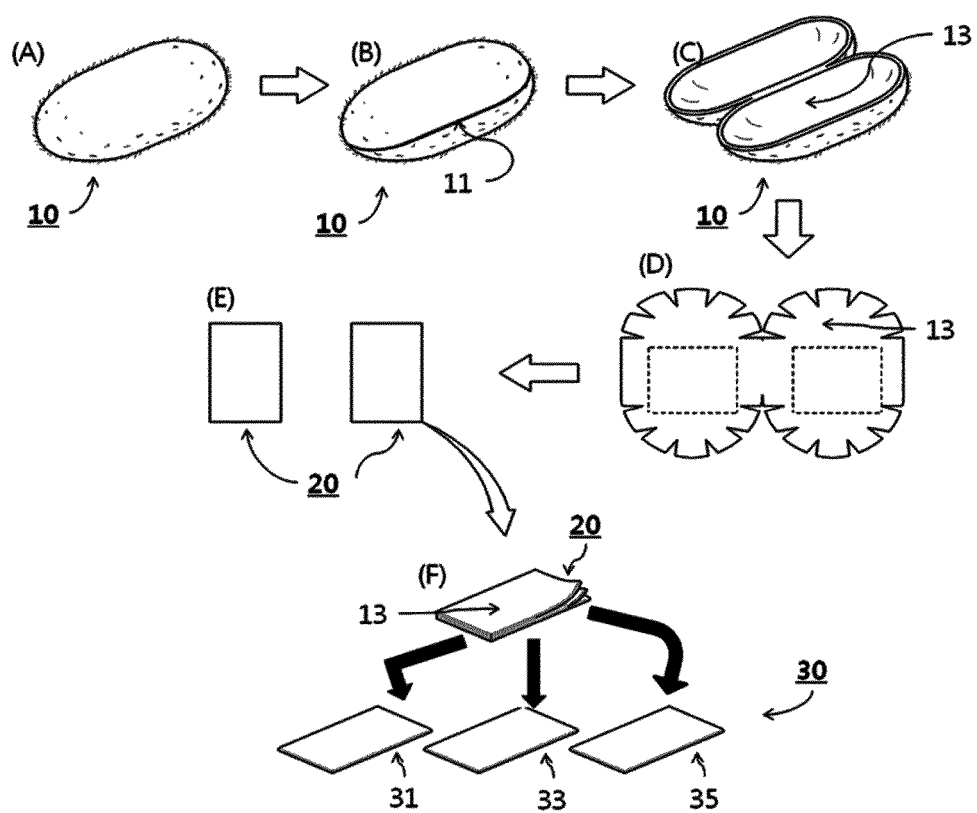
FIG. 1 is a schematic view illustrating a manufacturing procedure of a cocoon-based vascular patch according to one embodiment of the present invention.

With reference to FIG. 1, a method for manufacturing a cocoon-based artificial vascular patch in accordance with the present invention is explained, below.

1. Step 1: Preparation of Cocoon Fragment Having First Thickness.

As shown in FIG. 1A, a cocoon 10, the shell of which has a first thickness, is prepared.

A cocoon is a casting spun of silk by silkworms and is used as a material for silk fibers. In the present invention, cocoons, which may be unused resources, are up-cycled into a new high value-added product, thus bringing economic benefits to silkworm farmers. Naturally constructed by silkworms, which eat clean mulberry leaves, cocoons are free of toxicity and are suitable for use as an environment-friendly material.

Hence, the present invention takes a cocoon 10 as a material for vascular patches. The cocoon 10 is processed, as shown in FIGS. 1B to 1E, into two or more planar fragments, each having a first thickness.

In greater detail, the oval cocoon 10 is dissected along a cutting line 11 into halves, as shown in FIG. 1B. The dissected halves have semi-oval shapes, and are opened to expose the inside surface 13 of the cocoon, as shown in FIG. 10.

Next, the cocoon halves with curved inside surfaces 13 are planarized to some degree by cutting many sites along the edge as shown in FIG. 1D, and planar regions are cut out to obtain cocoon fragments 20 having a first thickness, as shown in FIG. 1E.

The vascular patches prepared in the present invention need not have a planar surface. Because a cocoon originally has an elliptical ball shape, the curved shape of the dissected cocoon may be utilized to yield curved vascular patches if necessary. For use as a small vascular patch, a cocoon fragment having a small area may be relatively planar. In contrast, when a relatively large area of the dissected cocoon halves is taken, the vascular patches may have curved surfaces.

Figure 2:
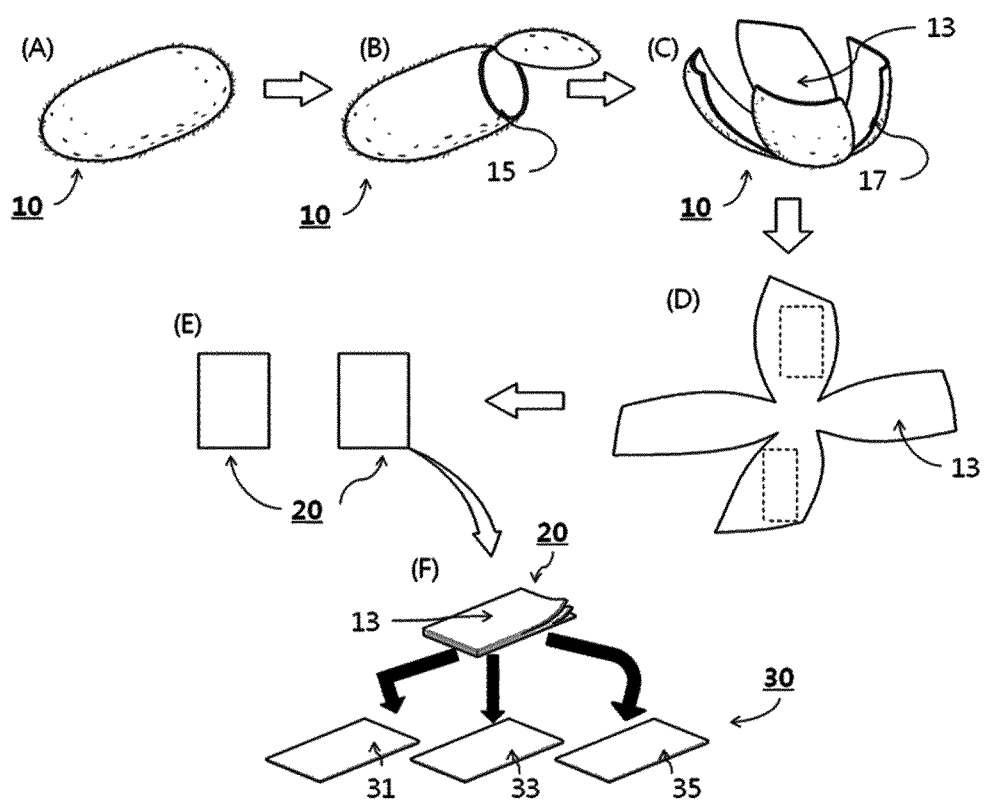
FIG. 2 is a schematic view illustrating the manufacturing procedure of a cocoon-based vascular patch according to a modified embodiment of the present invention.

With reference to FIG. 2, a modified method for preparing a cocoon fragment having a first thickness is described. In detail, an oval-shaped cocoon 10 is cut along a second cutting line 15 and a third cutting line 17 to expose the inside 13 of the cocoon 10, as shown in FIGS. 2B and 2C. Then, the dissected cocoon having a curved surface is spread as shown in FIG. 2D, and then cocoon fragments 20 having a first thickness are obtained as shown in FIG. 2E.

The preparation methods of cocoon fragments described in FIGS. 1 and 2 are only illustrative, but are not given as limitative embodiments. A cocoon fragment having a first thickness may be prepared by cutting a cocoon in the manners shown in FIGS. 1 and 2, but other cutting methods or orders may be used.

2. Step 2: Preparation of Cocoon Fragment Having Second Thickness (Vascular Patch)

Because the cocoon fragments 20 having a first thickness, prepared in step 1, have a multilayer structure identical to that of the cocoon shell, the multilayer structure may be split into thinner layers for use as a vascular patch.

Although the cocoon fragment 20 having a first thickness, prepared in step 1, is itself usable as a vascular patch, it is subjected to thickness splitting to give cocoon fragments 30 having a second thickness. In this regard, the second thickness is smaller than the first thickness. As mentioned above, the cocoon fragment having the first thickness may be itself used as a vascular patch without splitting to reduce the thickness thereof.

As they are, the cocoon fragments 30 can be applied as vascular patches. If necessary, they may be sterilized or chemically treated. For instance, the patches may be treated with 4-hexylresorcinol, an anti-thrombotic agent, to prevent thrombosis.

A cocoon shell varies in thickness (first thickness) from 0.3 to 1.0 mm depending on the silkworm species. In principal, any kind of cocoon may be used in the present invention.

For the purpose of the present invention, a cocoon having a shell thickness of 0.5~0.8 mm is employed. In the present invention, the cocoon shell is divided into inner, mid and outer strata. First, the outer stratum is defined as a layer corresponding to the outer 25% of the shell. The inner stratum is defined as a layer corresponding to the inner 15% of the shell. The other part corresponding to 60% of the total shell thickness, that is, the remaining middle cocoon shell except the outer and the inner layer is the mid stratum. That is, the outer stratum that spans from the outer surface to a point corresponding to 25% of the total shell thickness can be used as a cocoon fragment characterized by high elongation. The mid stratum that has a thickness corresponding to 60% of the total shell thickness exhibits high cell growth potential thanks to its high porosity. The inner stratum that accounts for the remaining 15% of the total shell thickness has a smooth surface and high tensile strength. In the present invention, any of inner, mid and outer strata of the cocoon fragment may be available, but the inner stratum is most preferable.

A cocoon fragment can be easily delaminated into up to 16 lamellas, although the number of delaminations is dependent on the shell thickness. The thicknesses of the lamellas can be determined according to the strength and elongation necessary for the kind and use of the vascular patch. From a cocoon having a shell thickness of 0.5~0.8 mm, in practice, a vascular patch 0.01 mm~0.7 mm thick can be prepared by delamination. As mentioned above, however, the cocoon fragment having the first thickness may be used as a vascular patch without delamination. According to the use of the vascular patch, selection may be made of cocoon fragments 30 having various thicknesses.

MODE FOR INVENTION

A better understanding of the present invention may be obtained through the following examples that are set forth to illustrate, but are not to be construed as limiting the present invention.

EXAMPLE 1

Preparation of Vascular Patch

The preparation of vascular patches according to the present invention started with sterilizing and washing a cocoon 10. The sterilized and washed cocoon 10 is cut at a proper site to expose the inside thereof. Then, the cut cocoon was further processed to planarize the curved interior.

Next, the planarized cocoon was cut into rectangular fragments 20, which were then peeled to remove the inner stratum accounting for the innermost surface 13 of the cocoon, followed by dividing the remainder into the mid stratum, and the outer stratum opposite to the inner stratum.

Mechanical properties of the cocoon-based vascular patches by cocoon stratum were measured. In this regard, a tensile test was conducted using a universal testing machine (DAEYEONG, Korea).

Test specimens with sizes of 2.5×0.07 (width×length) mm were used. The specimens were extended at a rate of 10 mm/min, with an initial gauge length set to be 10 mm.

Results are given in Table 1, below.

TABLE 1

| | Tensile Strength (MPa) | Elongation (%) |
|---|---|---|
| Inner Stratum (Ex. 1) | 60.20 ± 5.3 | 12.45 ± 1.5 |
| Mid Stratum (Ex. 3) | 46.19 ± 2.2 | 15.05 ± 1.7 |
| Outer Stratum (Ex. 2) | 29.36 ± 3.1 | 18.93 ± 1.3 |

As is understood from the data of Table 1, the cocoon-based vascular patches were different from one another in tensile strength and elongation by stratum. The highest tensile strength was detected in the inner stratum while the highest elongation was measured from the outer stratum.

In one embodiment of the present invention, 10 g of the inner stratum, higher in tensile strength than the other strata, was immersed for 24 hrs in a 3% solution of 4-hexylresorcinol, an anti-thrombotic agent. The 4-hexylresorcinol-impregnated inner stratum was left at 45° C. in an oven to evaporate the alcohol. After alcohol evaporation, the inner stratum weighed 10.3 g. The alcohol-vaporized cocoon inner stratum was sterilized with E. O. gas before use as a vascular patch.

Figure 3:
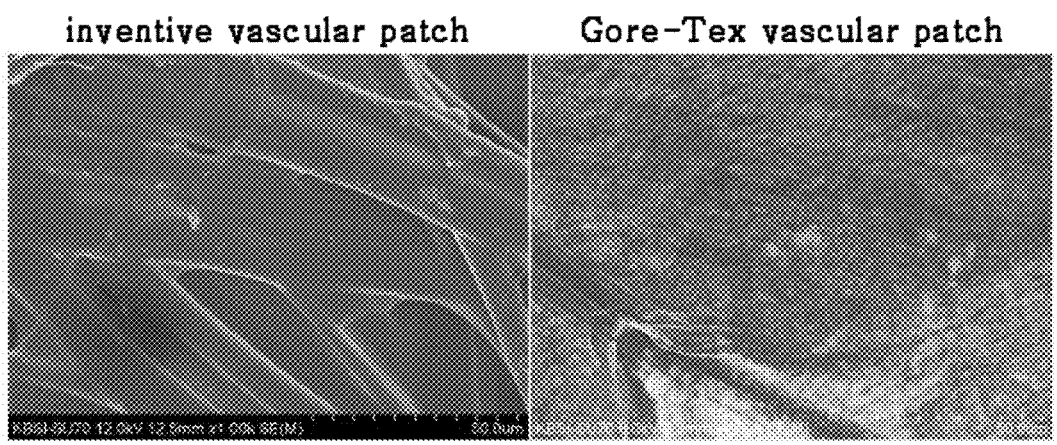
FIG. 3 shows morphologies of a cocoon-based vascular patch of the present invention and a Gore-Tex vascular patch as a control.

Morphologies of the vascular patch prepared above according to the present invention were observed by scanning electron microscopy (SEM), with a commercially available Gore-Tex patch used as controls for comparison, as shown in FIG. 3.

TEST EXAMPLE 1

Ultrasonic Analysis

1. Method
(1) Closure of Vascular Wall Defect

Vascular wall defects were closed with the cocoon-based vascular patch prepared in Example 1. Seven white rats were used as experimental animals. First, the white rats were shaved on the right neck to expose the skin covering the right carotid artery, and the skin was sterilized. Using microscissors, the right carotid artery was cut to form a vessel defect with dimensions of 0.5×1 mm. The defect was recovered with the cocoon-based vascular patch prepared above, followed by fixing the vascular patch with a 10-0 monofilament nylon thread (Ailee, Korea).

As control 1, a commercially available Gore-Tex vascular patch was used to close the vessel wall defect.

For comparison as control 2, the vessel wall defect was directly closed with a 10-0 monofilament nylon thread (Ailee, Korea).

Figure 4:
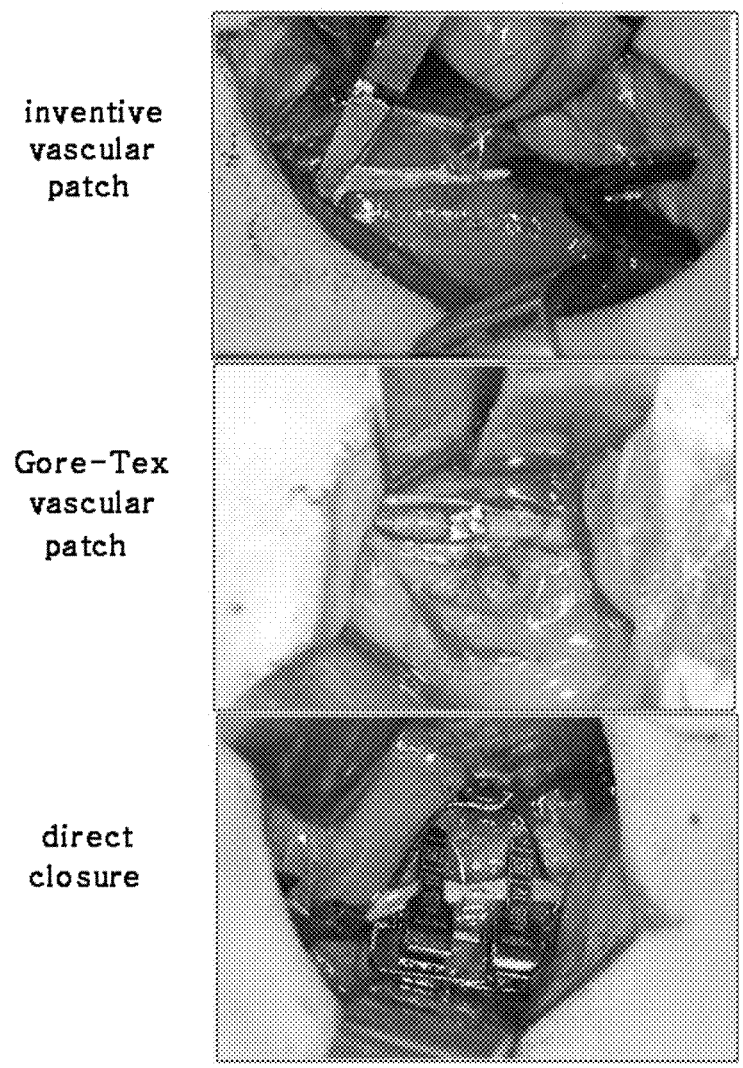
FIG. 4 shows images of closing vessel defects with the vascular patch of the present invention and the control Gore-Tex vascular path and of directly closing vessel defects.

FIG. 4 shows photographic images of closing vessel wall defects using respective methods.

(2) Ultrasonic Analysis Method

Ultrasonic analysis was conducted to examine whether the closed vascular defects allowed blood to pass therethrough or were stenosed. The blood vessels were measured for peak systolic velocity (PSV) by ultrasound assessment so as to check the functional regeneration of the vessels.

2. Test Results

Figure 5:
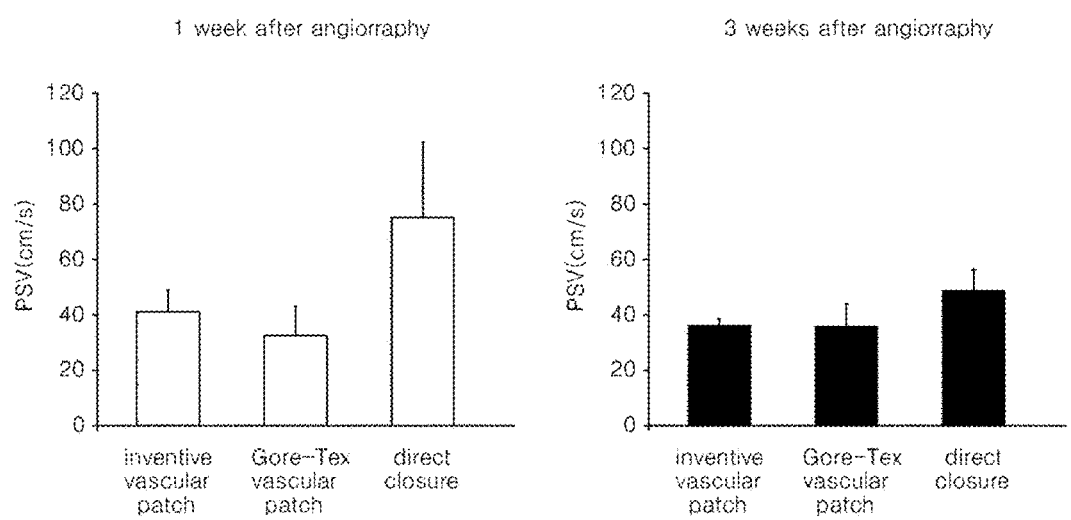
FIG. 5 compares peak systolic velocities of vessels one and three weeks after the closure of the vessel defects.

FIG. 5 compares PSV values of vessels one and three weeks after the closure of the vessel defects. One week after angiography, as can be seen in the graph of FIG. 5, the PSV was measured to be 41.20±7.92 cm/s for the vessel closed with the cocoon-based vascular patch, 32.74±10.50 cm/s for the vessel closed with the control 1 Gore-Tex vascular patch, and 75.23±27.05 cm/s for the directly closed vessel, with a statistical significance of p=0.007 thereamong as determined by ANOVA (Analysis of variance).

Three weeks after angiography, as can be seen in the graph of FIG. 5, the vessels were measured to have a PSV of 35.92±1.45 cm/s upon closure with the cocoon-based vascular patch of the present invention, 35.36±7.27 cm/s upon closure with the control 1 Gore-Tex vascular patch, and 48.36±6.15 cm/s upon direct closure as control 2. Statistical significance was determined at p=0.007 among the three groups as analyzed by ANOVA (Analysis of variance).

After transplantation of vascular patches, the vessels were monitored for PSV. After angiography with the vascular patch of the present invention, the external carotid artery of rats changed in PSV (cm/s) within a range of 20% or less, particularly, from 1 to 20%. Accordingly, the cocoon-based vascular patch of the present invention was evaluated to maintain the PSV stably.

TEST EXAMPLE 2

Angiographic Analysis of Change in Vascular Caliber

1. Test Method

Three weeks after angiography, angiography was carried out to examine whether the vessels functioned normally at the closed defects and to monitor a change in vessel diameter. To this end, 3 mg of a contrast agent (Visipaque™) was slowly introduced into the abdominal vena cava by intravenous injection (IV) using 21 gauge cannula, with the concomitant implement of angiography at the opposite carotid arteries. In this regard, wires were placed at positions mesiodistal to the vessel defect so as to indicate the position of the vessel defect.

Figure 6:
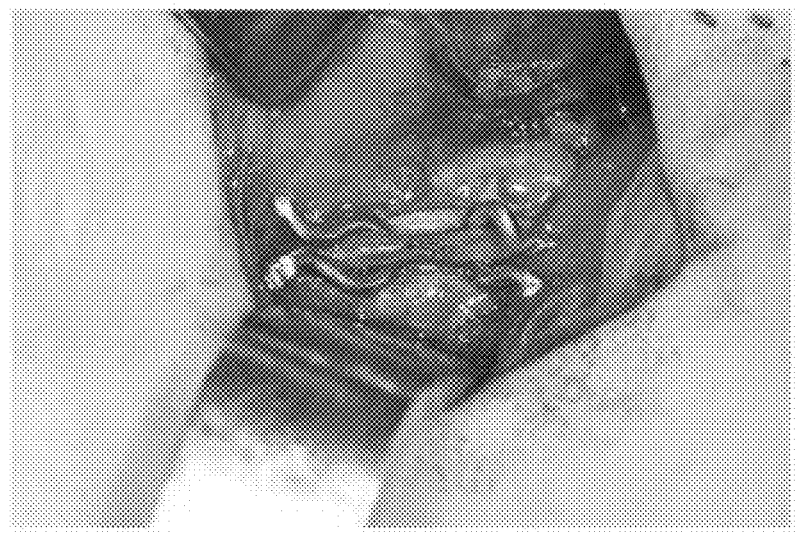
FIG. 6 is an image showing that wires are arranged mesiodistal to the vessel defects to indicate the positions of the vessel defects.

FIG. 6 is an image showing that wires are arranged mesiodistal to the vessel defect to indicate the position of the vessel defect.

2. Test Result

Figure 7:
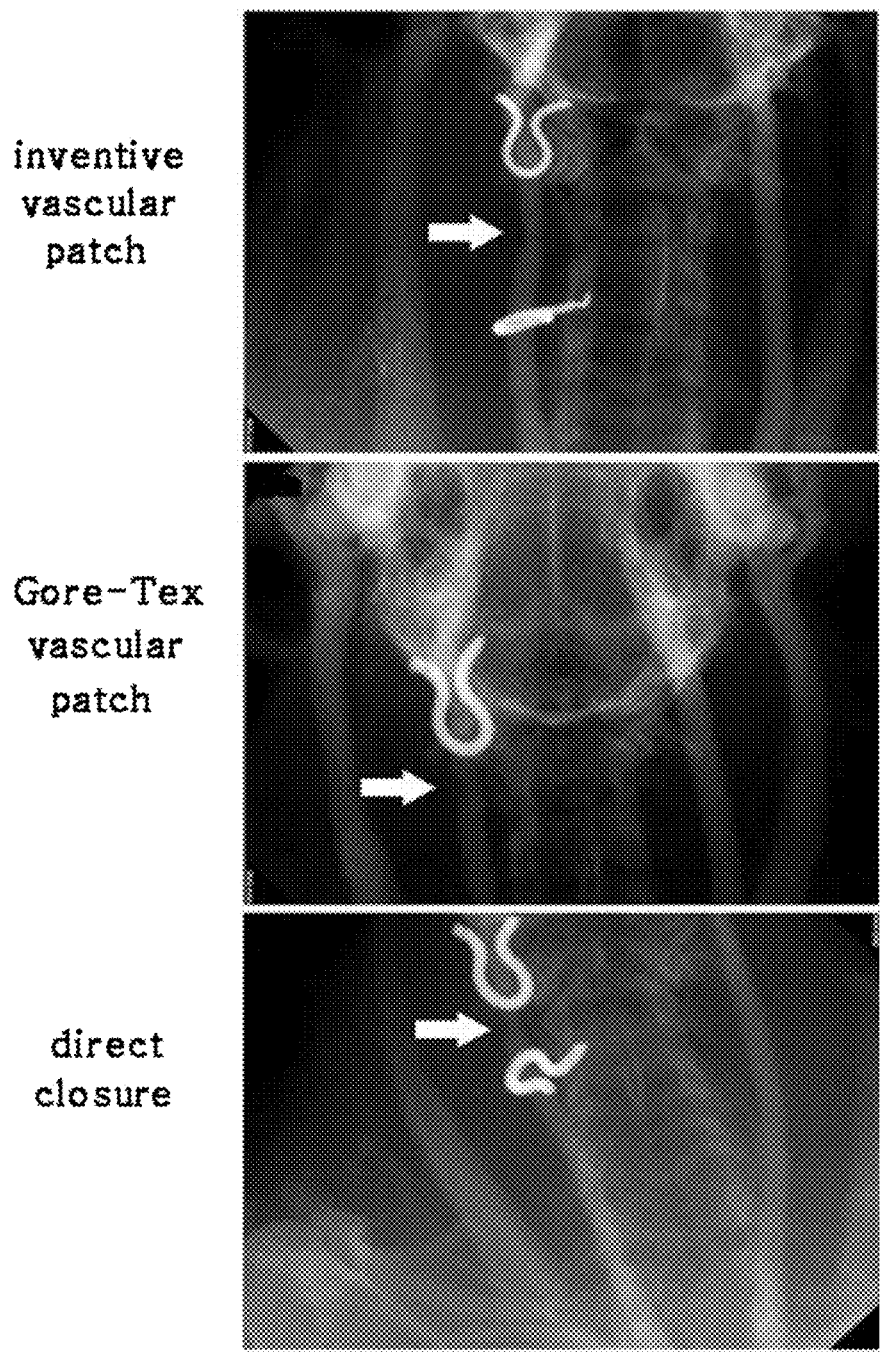
FIG. 7 shows angiograms of vessels 3 weeks after vessel defects were reconstructed with the vascular patch of the present invention, the conventional Gore-Tex vascular patch, and by direct closure.

Test results are shown in FIG. 7. In the angiograms, the closed vessel defect is indicated by white arrows while wires arranged over and below the defect appear white, indicating the position of the vessel defect. As can be seen, the vessel was found to retain its diameter better when the cocoon-based vascular patch of the present invention was used for the closure than the control 1 (Gore-Tex vascular patch), or the control 2 (the direct closure).

TEST EXAMPLE 3

Histological Assay

1. Test Method

Figure 8:
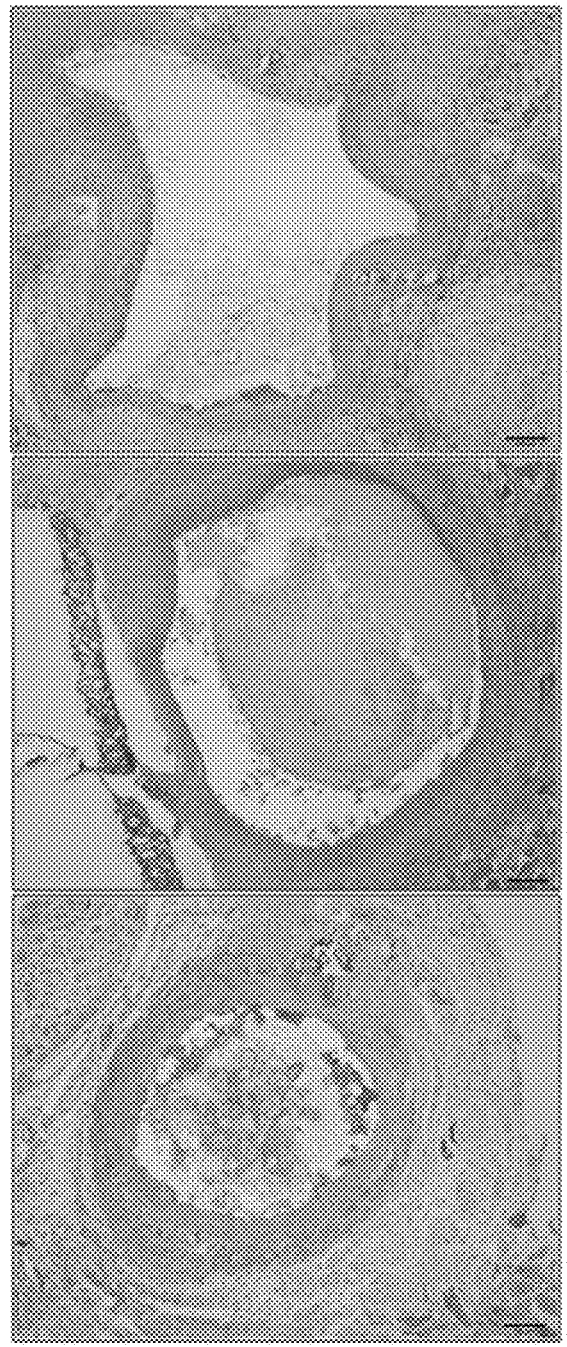
FIG. 8 shows images of cross sections of the vascular tissues two weeks after vessel defects were reconstructed with the vascular patch of the present invention, with the Gore-Tex vascular patch, and after direct closure.

A histological assay was conducted to examine the wall thickness and diameter of the vessel at the defect, and a foreign body reaction attributed to the vascular patch. A vessel including the defect closed with the vascular patch was dissected while the opposite ends of the vessel were ligatured to retain blood therein, thereby retaining the diameter of the vessel. The vascular specimen thus obtained was fixed with alcohol, and stained with hematoxylin and eosin. The fixed, stained vascular specimen was cross sectioned before observation. FIG. 8 shows images of cross sections of the vascular tissues two weeks after closure with the vascular patch of the present invention and the Gore Tex patch as the control 1, and after direct closure as control 2.

2. Test Result

As can be seen in FIG. 8, the histological observation demonstrated that no particular foreign body reactions were around the cocoon-based vascular patch of the present invention and that the reconstructed vessel wall was not particularly discerned from adjacent tissues, with the inner diameter of the vessel kept constant. The control vessel in which the Gore Tex vascular patch was used, although maintaining the inner diameter generally well, exhibited the overgrowth of the internal vessel wall in some specimens. On the other hand, severe stenosis was observed in the directly closed vessel.

Taken together, the data obtained above demonstrate that the vascular patch according to the present invention significantly reduces vessel wall overgrowth and stenosis, compared to conventional Gore Tex vascular patches and direct closure, thereby effectively maintaining the blood circulation and the vessel diameter.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

DESCRIPTION OF NUMERICAL REFERENCES IN DRAWINGS

10: Cocoon
11: Cutting line 1
13: Inside surface
15: Cutting line 2
17: Cutting line 3
20: Cocoon fragment with a first thickness
30: Cocoon fragment with a second thickness
31: Inner stratum
33: Mid stratum
35: Outer stratum

The invention claimed is:

1. A method for manufacturing a biocompatible cocoon-based vascular patch without requiring removal of the biocompatible cocoon-based vascular patch after application thereof, comprising:
dividing a cocoon into two or more fragments in a predetermined form, the cocoon having a shell with a first thickness;
conducting at least one round of sterilization for the two or more fragments; and
applying one of the two or more sterilized fragments to a vascular wall defect of a subject,
wherein after the applying step, the one of the two or more fragments is not required to be removed from the vascular wall defect of the subject.

2. The method of claim 1, further comprising delaminating each of the fragments into a lamellar fragment with a second thickness, the second thickness being less than the first thickness.

3. The method of claim 2, further comprising packing the fragments of the second thickness prepared in the delaminating step.

4. The method of claim 2, wherein the lamellar fragment with the second thickness is an inner stratum of the cocoon.

5. The method of claim 2, wherein the lamellar fragment with the second thickness is a mid stratum of the cocoon.

6. The method of claim 2, wherein the lamellar fragment with the second thickness is an outer stratum of the cocoon.

\* \* \* \* \*